US012741052B2

(12) United States Patent
Hansson et al.

(10) Patent No.: US 12,741,052 B2
(45) Date of Patent: Sep. 22, 2026

(54) WOUND CARE PRODUCT COMPRISING AN ANTIMICROBIAL COATING

(71) Applicant: Mölnlycke Health Care AB, Gothenburg (SE)

(72) Inventors: Dennis Hansson, Gunnilse (SE); Océane Lançon, Säve (SE)

(73) Assignee: Mölnlycke Health Care AB, Mölndal (SE)

( * ) Notice: Subject to any disclaimer, the term of this patent is extended or adjusted under 35 U.S.C. 154(b) by 238 days.

(21) Appl. No.: 18/552,458

(22) PCT Filed: Apr. 7, 2022

(86) PCT No.: PCT/EP2022/059209
§ 371 (c)(1),
(2) Date: Sep. 26, 2023

(87) PCT Pub. No.: WO2022/223305
PCT Pub. Date: Oct. 27, 2022

(65) Prior Publication Data

US 2024/0181121 A1 Jun. 6, 2024

(30) Foreign Application Priority Data

Apr. 20, 2021 (EP) .................................... 21169366

(51) Int. Cl.

| | |
|---|---|
| ***A61L 15/44*** | (2006.01) |
| ***A61F 13/02*** | (2024.01) |
| ***A61F 13/0246*** | (2024.01) |
| ***A61L 15/58*** | (2006.01) |

(52) U.S. Cl.
CPC ............ *A61L 15/44* (2013.01); *A61F 13/023* (2013.01); *A61F 13/0253* (2013.01); *A61L 15/58* (2013.01); *A61L 2300/206* (2013.01); *A61L 2300/404* (2013.01)

(58) Field of Classification Search
CPC .... A61L 15/44; A61L 15/58; A61L 2300/206; A61L 2300/404; A61L 15/46; A61F 13/023; A61F 13/0253
See application file for complete search history.

(56) References Cited

U.S. PATENT DOCUMENTS

2013/0239977 A1* 9/2013 McGuire, Jr. ........... A61L 24/06 424/405
2017/0095431 A1* 4/2017 Andrews .............. A61K 9/7084

FOREIGN PATENT DOCUMENTS

| | | | |
|---|---|---|---|
| EP | 2995324 A1 * | 3/2016 | ............. A61L 15/26 |
| EP | 2996468 | 3/2016 | |
| EP | 3191039 | 7/2017 | |
| EP | 3191144 | 7/2017 | |
| WO | WO 2011/009083 | 1/2011 | |
| WO | WO 2019/241391 | 12/2019 | |

OTHER PUBLICATIONS

Wiegand et al.; "pH Influence on Antibacterial Efficacy of Common Antiseptic Substances"; Skin Pharmacology and Physiology; vol. 28, Issue 3; pp. 147-158. Published Apr. 2015 (Year: 2015).*
Barbour et al.; "Synthesis, characterization, and efficacy of antimicrobial chlorhexidine hexametaphosphate nanoparticles for applications in biomedical materials and consumer products"; Int. J. Nanomedicine; 2013:8, pp. 3507-3519. Published Aug. 18, 2013. (Year: 2013).*
International Search Report and Written Opinion were mailed on Jul. 12, 2022 by the International Searching Authority for International Application No. PCT/EP2022/059209 filed on Apr. 7, 2022 and published as WO2022223305 (Applicant—Molnlycke Health Care AB) (10 pages).
Duckworth et al., "Alginate films augmented with chlorhexidine hexametaphosphate particles provide sustained antimicrobial properties for application in wound care", Journal of Materials Science: Materials in Medicine, vol. 31, No. 3, 2020.

* cited by examiner

*Primary Examiner* — Jeffrey T. Palenik
(74) *Attorney, Agent, or Firm* — Ballard Spahr LLP

(57) ABSTRACT

Described is a wound care product having a backing layer and an adhesive layer having a skin-facing surface, wherein at least a portion of the skin-facing surface of the adhesive layer has an antimicrobial coating.

13 Claims, 6 Drawing Sheets

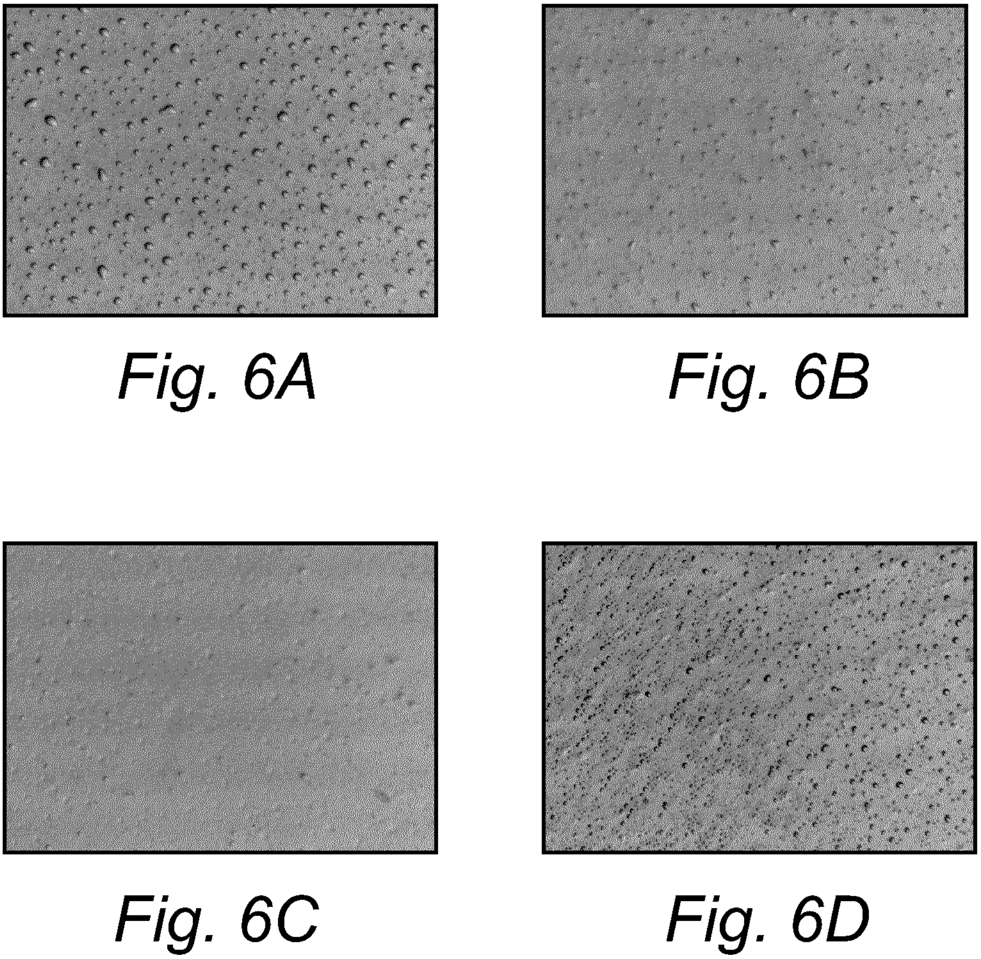
Fig. 6A
Fig. 6B
Fig. 6C
Fig. 6D
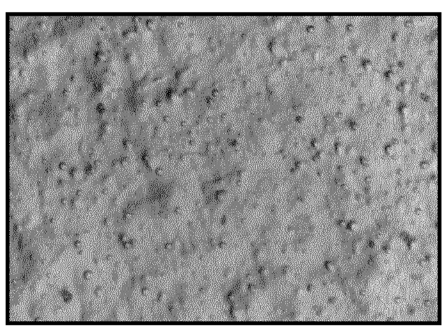
Fig. 7

WOUND CARE PRODUCT COMPRISING AN ANTIMICROBIAL COATING

CROSS REFERENCE TO RELATED APPLICATIONS

This application is a U.S. National Phase Application of International Application No. PCT/EP2022/059209, filed Apr. 7, 2022, which claims priority to European Patent Application No. 21169366.8, filed Apr. 20, 2021, each of which are hereby incorporated by reference in their entirety.

TECHNICAL FIELD

The present disclosure generally relates to a wound care product comprising a backing layer and an adhesive layer having a skin-facing surface, wherein at least a portion of the skin-facing surface of the adhesive layer comprises an antimicrobial coating.

BACKGROUND

Infection is a common problem in chronic and surgical wounds. A surgical site or an open wound is a suitable environment for bacteria to accommodate and colonize. A bacterial infection in the wound or at the skin surrounding the wound may disrupt the normal wound healing process and result in chronic, non-healing wounds.

In wound treatment, antimicrobial agents are often used to eliminate or reduce infection of the wound. The incorporation of antimicrobial agents into bandages and wound dressings may promote healing and eliminate or reduce the risk of infection of the wound. To that end, various types of antimicrobial dressings have been developed.

In a surgical setting, so called incision drapes may be utilized to isolate the surgical site from non-sterile areas that could increase the risk for surgical site infections. An incision drape is designed to be cut through during surgery.

In both a surgical setting and in the treatment of wounds, infection caused by contaminating microorganisms needs to be prevented.

For many wound care products, a quick delivery of antimicrobial agents is desirable. The reason for this is that a slow and gradual release of antimicrobial agents can cause the bacteria present at the wound site or at the skin to adapt to a generally low antimicrobial concentration.

Wound care products, such as dressings and incision drapes typically comprise a self-adhering adhesive, also known as pressure-sensitive adhesive (PSA), which purpose is to adhere to the wound and/or to the skin surrounding the wound and thus to fixate the dressing in a desirable position. Various adhesives may be used for affixing the wound care products on the skin, some of the most common being acrylic adhesives, silicone-based adhesives and hot melt adhesives. During assembly of the wound care product, the adhesive layer is typically covered by a release liner to protect the adhesive layer and the product from contamination prior to use. The products are typically sterilized prior to use in a surgical setting or before being applied to the skin or wound of a patient.

In order to enable a quick release, and thereby a quick effect, the skin-facing surface of the adhesive layer may be coated with an antimicrobial composition.

Antimicrobial dressings comprising soluble silver salt coatings on the adhesive surface are known from e.g. EP 3 191 039A1 and EP 3 191 144B1. In these dressings, silver is released as positively charged ions when in contact with liquid. While the release of silver has an antimicrobial effect and may reduce the bacterial concentration at the wound site, its effect against against fungi, e.g. *Candida albicans,* as well as the prevention and elimination of bacterial biofilms is restricted.

Chlorhexidine is another antimicrobial compound, commonly used as a wound cleanser prior to surgery. Chlorhexidine has also been used in oral applications, such as mouth rinses, and has also been applied to medical devices, such as dental implants and catheters. Chlorhexidine is considered environmentally sound and safe. The most commonly used chlorhexidine salts are chlorhexidine gluconate and chlorhexidine acetate.

When applying an antimicrobial coating to the adhesive layer of a wound care product, it is important that the coating does not impair the adhesion properties or the "tackiness" of the adhesive layer.

Furthermore, it is important that the antimicrobial coating remains on the adhesive surface of the wound care product when the product is to be applied to the skin or wound of a patient. One problem associated with wound care products comprising antimicrobial coatings is that once the release liner is removed from the wound care product, the antimicrobial composition is removed with the release liner, and thereby removed from the adhesive layer. As a consequence, the antimicrobial effect of the dressing is eliminated or at least significantly reduced.

It is therefore a need to overcome the above mentioned challenges with antimicrobial wound care products. More particularly, there is a need to provide a wound care product that provides a quick delivery of an antimicrobial compound, wherein the effect remains in the wound care product even after disassembly of the product; i.e. even after the removal of the release liner.

SUMMARY

In view of the above mentioned problems, it is an object of the present disclosure to provide improvements with respect to antimicrobial wound care products, particularly with respect to providing a product comprising a soluble antimicrobial coating, wherein such coating remains on the adhesive layer after the release liner has been removed from the product.

According to a first aspect, there is provided a wound care product comprising a backing layer and an adhesive layer having a skin-facing surface, wherein at least a portion of the skin-facing surface of the adhesive layer comprises an antimicrobial coating, wherein the coating is soluble in an aqueous medium and wherein the coating comprises chlorhexidine phosphate.

The antimicrobial coating is soluble in an aqueous medium. Accordingly, in contact with wound exudate or moist skin, the antimicrobial coating dissolves and allows for a quick initial release of chlorhexidine phosphate such that bacteria present at the wound or surgical site or at the skin surrounding the wound or incision can be eradicated. Growth of infecting microorganisms at the surface of the adhesive layer is thereby prevented, which avoids colonization at the wound site and within the wound care product.

The present disclosure is based on the realization that an antimicrobial coating comprising chlorhexidine phosphate can be easily applied onto the adhesive layer of a wound care product, for example by means of spray coating, without impairing the adhesive properties of the adhesive layer. More importantly, the antimicrobial coating of the present disclosure has the ability to remain on the skin-facing surface of the adhesive layer even after removal of the release liner.

While many antimicrobial compounds may be provided as coatings on the adhesive skin contact layer of a wound care product, and may also possess an antimicrobial activity against various types of bacteria, many coatings suffer from problems with transfer of the antimicrobial coating from the adhesive surface to the release liner. As a consequence, the antimicrobial effect is lost within the dressing.

Chlorhexidine is a safe and powerful antimicrobial agent. The inventors have tested various types of chlorhexidine salts, with the conclusion that chlorhexidine phosphate (CHP) has both the ability to remain on the adhesive layer after removal of the release liner, and furthermore the ability to dissolve readily in contact with wound exudate. The surprising finding that a soluble coating comprising chlorhexidine phosphate remains on the adhesive layer; i.e. within the wound care product, renders the product of the present disclosure a commercially attractive solution to prevent infections from occurring in wounds and at surgical sites.

The present inventors have also compared the antimicrobial activity of chlorhexidine phosphate (CHP) with other antimicrobial agents known in the art, with the conclusion that CHP is surprisingly effective against both gram negative and gram positive bacteria as well as *Candida albicans*. Furthermore, CHP is effective against bacterial biofilms.

In embodiments, at least 60%, preferably at least 80% of the antimicrobial coating is configured to be dissolved within 3 hours of exposure to an aqueous medium.

Accordingly, a rapid antimicrobial effect can be established at the wound site, and the antimicrobial coating is completely dissolved in contact with wound exudate.

In embodiments, the wound product comprises a release liner, wherein the release liner is detachably attached to the skin facing surface of the adhesive layer.

The purpose of the release liner is to protect the dressing and the adhesive layer from contamination. The release liner is applied after the product has been manufactured, and is removed prior to application of the dressing onto a dermal surface.

The wound care product may be a dressing, such as a wound dressing or a surgical drape, preferably an incision drape.

Dressings are typically applied to an open wound or a scar in need of treatment. Incision drapes are applied during surgery and are designed to be cut through. For both types of products, prevention of infectious microorganisms at the wound or skin site is desirable.

In embodiments where the wound care product is an incision drape, the adhesive layer may comprise a polyacrylate based adhesive.

It is, however, conceivable that the adhesive layer of the drape comprises other types of adhesives, such as silicone based adhesives.

In embodiments where the wound care product is a dressing, the adhesive layer preferably comprises a silicone based adhesive.

Such an adhesive is gentle to the skin and allows the dressing to be removed and re-applied without harming the skin.

In embodiments, the antimicrobial coating is a discontinuous coating on the skin-facing surface of the adhesive layer.

Accordingly, the antimicrobial coating does not fully cover the surface of the skin-facing surface of the adhesive layer. This is beneficial to avoid impairing the adhesion to the skin afforded by the adhesive layer. Such a discontinuous coating may e.g. be provided by means of spray coating.

A discontinuous coating enables a good balance between a sufficient release of chlorhexidine phosphate, as well as maintaining the adhesive properties of the adhesive layer.

In embodiments, the concentration of chlorhexidine phosphate in the coating is from 5 to 1000 $\mu g/cm^2$, e.g. from 10 to 500 $\mu g/cm^2$, e.g. from 20 to 200 $\mu g/cm^2$.

Accordingly, a sufficient release of the antimicrobial; i.e. chlorhexidine phosphate is enabled when the coating dissolves in contact with wound fluid or skin moisture. Furthermore, this range provides for a good balance between a sufficient release of chlorhexidine phosphate, as well as maintaining the adhesive properties of the adhesive layer.

A dressing of the present disclosure may either be absorbent or non-absorbent.

In embodiments where the dressing is non-absorbent, the dressing comprises a backing layer and an adhesive skin contact layer. Such a dressing may be useful in various applications. For example, people suffering from epidermolysis bullosa, a disease (or group of diseases) characterized by mechanical fragility of the skin and mucous membranes, may be treated by applying silicone based adhesive dressings. Infection prevention is an important element of the treatment.

In alternative embodiments, the wound care product is an absorbent dressing. In such embodiments, the dressing further comprises an absorbent pad arranged between the backing layer and the adhesive layer.

Since many wounds, particularly infected wounds, may exude large amounts of exudate, it is typically necessary to utilize a dressing comprising an absorbent pad. The absorbent pad may comprise any absorbent material, such as absorbent fibers, gels, foams etc. Preferably, the absorbent pad comprises a hydrophilic foam, e.g. a hydrophilic polyurethane foam. The absorbent pad may comprise one or more pad-forming layers.

The dressing of the present disclosure may be utilized in all wound care scenarios where an antimicrobial effect is desired. The dressing may e.g. be utilized in negative pressure wound therapy (NPWT) applications. In these cases, the dressing is connected to a negative pressure source, e.g. a pump, which applies a negative pressure, e.g. vacuum through the dressing. The dressing, when used in negative pressure wound therapy, may be absorbent or non-absorbent. In the latter case, the dressing may act as a secondary dressing and is typically used in conjunction with a wound filler, e.g. a gauze or a foam which is first applied to the open cavity wound.

In order to enhance the antimicrobial effect of the dressing, the absorbent pad may comprise at least one second antimicrobial compound.

The provision of a second antimicrobial compound in the pad is typically associated with a slower, more gradual release of antimicrobial compared to the quicker release provided by the soluble antimicrobial coating. For various applications, it may be desirable to design the product such that a quick kill-off of bacteria is achieved by means of the coating, and a slower release is achieved by means of the antimicrobial present in the absorbent pad.

In embodiments, the adhesive layer comprises at least one third antimicrobial compound. In other words, the adhesive layer of the dressing or the incision drape may comprise an antimicrobial compound. The provision of an antimicrobial in the adhesive layer is associated with a slower release and is advantageously combined with the quick release implied by the soluble antimicrobial coating. Additional excipients may be required within the adhesive layer to facilitate the release of the third antimicrobial compound from the adhesive layer.

The second and the third antimicrobial compound may be the same or different. The at least one second and third antimicrobial compounds may be chlorhexidine phosphate.

According to another aspect, there is provided a method of manufacturing a wound care product comprising:

a) providing a wound care product comprising a backing layer and an adhesive layer having a skin-facing surface, wherein the wound care product optionally comprises an absorbent pad arranged between the backing layer and the adhesive layer,
b) providing an aqueous solution of chlorhexidine phosphate by dissolving chlorhexidine in phosphoric acid and water,
c) applying the aqueous solution onto at least a portion of the skin-facing surface of the adhesive layer,
d) drying the aqueous solution on the skin facing surface of the adhesive layer.

The method of the present disclosure allows for a simple, yet efficient method for manufacturing an antimicrobial wound care product.

The aqueous solution is provided by dissolving chlorhexidine in phosphoric acid and water. Accordingly, a dissolved solution of chlorhexidine phosphate is obtained.

During the drying step, the water phase of the coating is removed. However, in contact with skin moisture or wound fluid, the dried coating dissolves and chlorhexidine phosphate can be released into the wound and to the skin surrounding the wound.

In embodiments, the pH of the aqueous solution of chlorhexidine phosphate is from 4 to 6.

Infectious bacteria typically thrive at higher pH values, such as around 7.5 to 8.5. The low pH of the coating solution may therefore yield an environment unsuitable for infectious bacteria to grow and colonize, and may also render the bacteria more sensitive to the antimicrobial effect provided by chlorhexidine phosphate.

The aqueous solution may be applied onto at least a portion of the skin-facing surface of the adhesive layer by any means known to the skilled person.

Preferably, the aqueous solution is applied onto at least a portion of the skin facing surface of the adhesive layer by means of spray coating.

Spray coating is a simple coating method associated with various advantages. For example, the fact that the solution can be sprayed onto the adhesive surface gives a more controlled application of the coating. It is possible to concentrate the application in particular areas of the dressing and to control the size of the droplets on the skin-facing surface.

Furthermore, the solution can be applied in a manner which does not adversely affect the adhesive properties of the adhesive layer.

In embodiments, the method further comprises the step of e) applying a release liner to the skin-facing surface of the adhesive layer.

The release liner is configured to be detachably attached to the adhesive layer (and the coating) and is configured to be removed prior to application of the dressing onto the skin or wound of a patient.

Further features of, and advantages with, the present disclosure will become apparent when studying the appended claims and the following description. The skilled addressee realizes that different features of the present disclosure may be combined to create embodiments other than those described in the following, without departing from the scope of the present disclosure.

BRIEF DESCRIPTION OF DRAWINGS

The various aspects of the present disclosure, including its particular features and advantages, will be readily understood from the following detailed description and the accompanying drawings, in which:

FIG. 6*a* is a light microscopy image of the skin facing surface of a wound contact layer comprising an antimicrobial chlorhexidine phosphate (CHP) coating after sterilization and after removal of the release liner.

FIG. 6*b* is a light microscopy image illustrating the release liner removed from the wound contact layer of FIG. 6*a*.

FIG. 6*c* is a light microscopy image of the skin facing surface of a wound contact layer comprising an antimicrobial chlorhexidine gluconate (CHG) coating after sterilization and after removal of the release liner.

FIG. 6*d* is a light microscopy image illustrating the release liner removed from the wound contact layer of FIG. 6*c*.

FIG. 7 is a light microscopy image of the skin facing surface of an incision drape comprising an antimicrobial chlorhexidine phosphate (CHP) coating after sterilization and after removal of the release liner.

DETAILED DESCRIPTION

The present disclosure will now be described more fully hereinafter with reference to the accompanying drawings, in which currently preferred embodiments of the present disclosure are shown. The present disclosure may, however, be embodied in many different forms and should not be construed as limited to the embodiments set forth herein; rather, these embodiments are provided for thoroughness and completeness, and fully convey the scope of the present disclosure to the skilled person.

Figure 1:
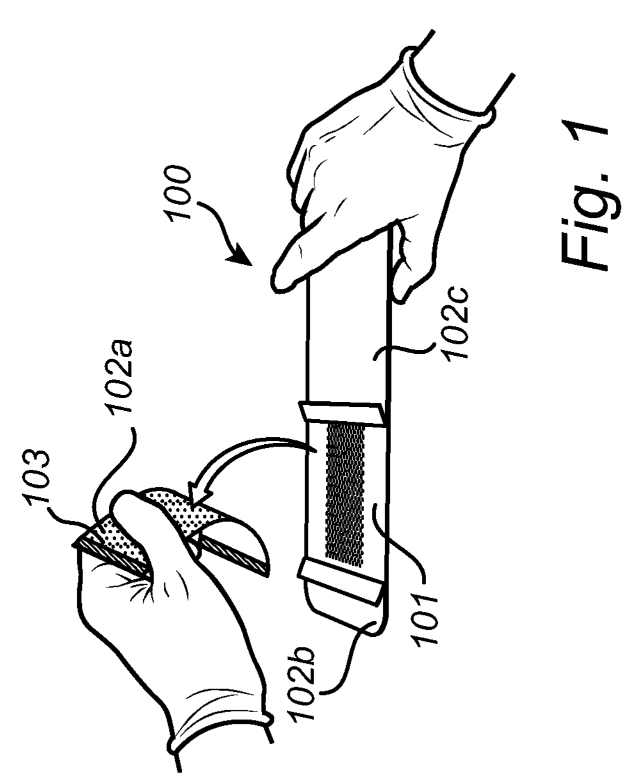
FIG. 1 conceptually illustrates the problem associated with dressings of the prior art.

The problem underlying the present disclosure is schematically illustrated in FIG. 1. FIG. 1 illustrates a dressing 100 according to the prior art comprising an adhesive skin contact layer 101 and a release liner 102. The release liner illustrated in FIG. 1 comprises three releasable portions 102*a-c*, and is attached to the adhesive skin contact layer 101 of the dressing. The adhesive skin contact layer 101 initially comprises an antimicrobial coating on the skin-facing surface. When a first release liner portion 102*a* is removed, the antimicrobial coating is removed from the adhesive skin contact layer 101 (illustrated by the arrow in FIG. 1), and transferred to the surface of the release liner portion (see 103). Consequently, the antimicrobial effect of the dressing is eliminated.

Figure 2:
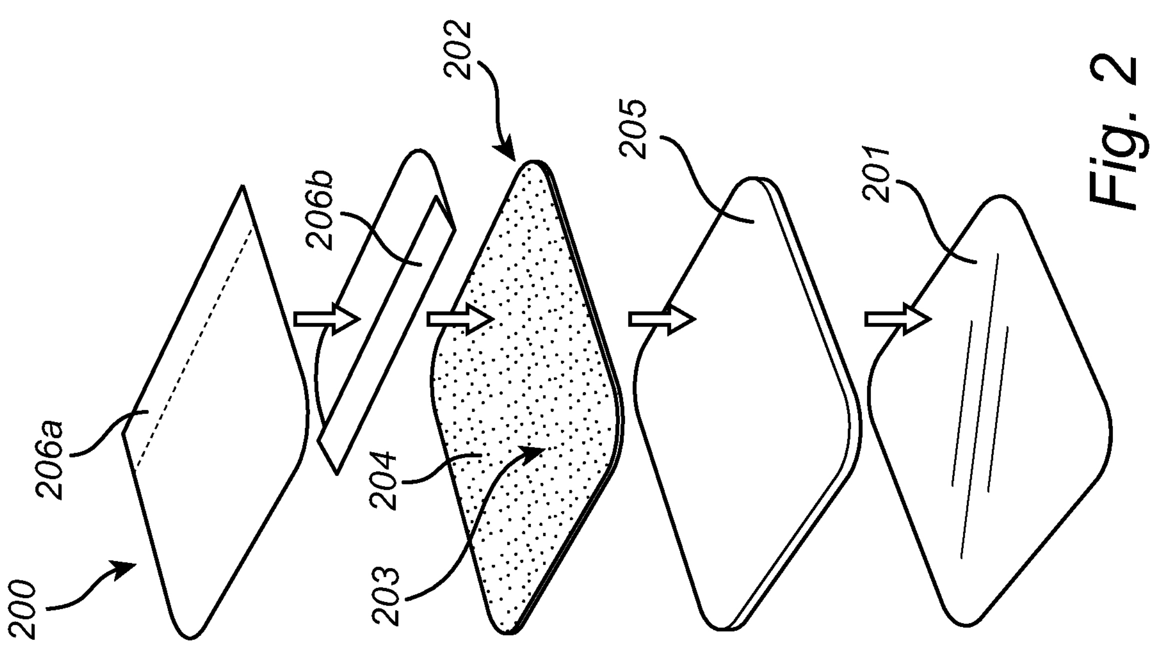
FIG. 2 illustrates a split view of a dressing according to an exemplary embodiment of the present disclosure.

In FIG. 2, a wound care product according to an exemplary embodiment is conceptually illustrated. The wound care product is a dressing 200 comprising a backing layer 201 and an adhesive layer 202 having a skin-facing surface 203, wherein at least a portion of the skin-facing surface 203 of the adhesive layer 202 comprises an antimicrobial coating 204, wherein the antimicrobial coating 204 is soluble in an aqueous medium and wherein the coating 204 comprises chlorhexidine phosphate.

The adhesive layer as an opposing surface (not shown) facing the backing layer 201.

Chlorhexidine has the following chemical structure:

initially applied as an aqueous solution to the surface of the adhesive layer, and subsequently dried. In contact with wound exudate or an aqueous medium, the dried coating will be dissolved and released from the adhesive layer.

In embodiments, at least 60%, preferably at least 80% of the antimicrobial coating (204) is configured to be dissolved within 3 hours of exposure to an aqueous medium.

In embodiments, at least 90%, e.g. 100% of the antimicrobial coating (204) is configured to be dissolved within 3 hours of exposure to an aqueous medium.

Accordingly, the antimicrobial coating of the present disclosure allows for a rapid release of the active antimicrobial agent (CHP) and a rapid antimicrobial effect.

The antimicrobial coating of the present disclosure comprises a dissolved chlorhexidine phosphate salt. In other words, when the coating is applied, typically in the form of an aqueous solution, substantially no undissolved CHP particles are present. This is to enable a quick dissolution (and a rapid effect) in contact with wound exudate.

The present inventors have found that chlorhexidine phosphate is not only efficient in killing gram positive and gram negative bacteria, but is also efficient against *Candida albicans* (see Example 1). Accordingly, the wound care product of the present disclosure represents a promising and

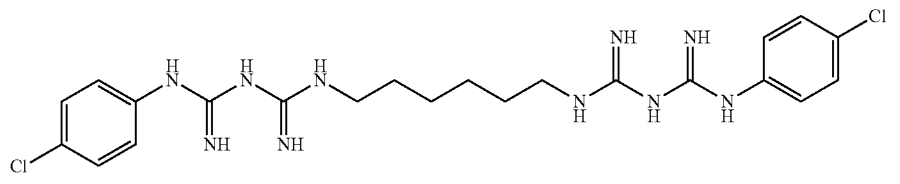 [SMILES: N=C(NCCCCCCNC(=N)NC(=N)Nc1ccc(Cl)cc1)NC(=N)Nc1ccc(Cl)cc1]

The phosphate counter-ion and has the following chemical structure:

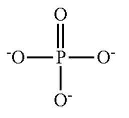

In the embodiment illustrated in FIG. 2, the dressing 200 comprises an absorbent pad 205 arranged between the backing layer 201 and the adhesive layer 202. Accordingly, the dressing 200 is absorbent. The adhesive layer 202 may e.g. be coated on the absorbent pad 205 or it may be adhered or laminated to the absorbent pad 205.

The adhesive layer comprises a soluble coating 204 comprising chlorhexidine phosphate on the skin-facing surface 203.

Preferably, at least 60%, e.g. at least 80% of the skin facing surface of the adhesive layer comprises an antimicrobial coating.

When the antimicrobial coating 204 is exposed to wound exudate, it dissolves and chlorhexidine phosphate is released to the wound site. A rapid antimicrobial effect can thereby be achieved.

As used herein, the term "soluble in an aqueous medium" means that the coating dissolves in contact with an aqueous medium. The aqueous solution may be water.

Accordingly, the antimicrobial coating dissolves quickly in contact with wound exudate or skin moisture. Even low amounts of skin moisture or wound exudate will induce dissolution of the antimicrobial coating. The coating is commercially viable antimicrobial product that can be used against several microbial species. The wound care product also satisfies the stricter (governmental) requirements that antimicrobial wound care products must fulfil when commercialized.

Moreover, the inventors have found that, compared to other commercially available chlorhexidine salts (and other antimicrobial agents), a coating comprising chlorhexidine phosphate has the ability to remain on the skin-facing surface 203 of the adhesive layer 202 of the dressing even when the release liner is removed from the dressing. Accordingly, the antimicrobial effect remains within the dressing upon removal of the release liner.

The release liner in FIG. 2 comprises two release liner portions 206*a* and 206*b*. The first release liner portion 206*a* is arranged above the second release liner portion 206*b*. The second release liner portion 206*b* is folded over itself and the first release liner portion 206*a* overlaps and extends beyond the folded edge of the second release liner portion 206*b*. Accordingly, a first and a second tab are formed, which the caregiver or patient can grasp to remove the release liner in a facilitated manner.

Without wishing to be bound by theory, it is believed that the less hygroscopic nature of chlorhexidine phosphate compared to, for instance, chlorhexidine gluconate is a contributing factor to the substantially lower transfer of chlorhexidine phosphate from the adhesive layer to the release liner.

The absorbent pad 205 is not limited to a specific material, but any absorbent material may be utilized. Preferably, the absorbent pad 205 comprises a foam, such as a polyurethane foam.

A dressing comprising a polyurethane foam pad is capable of absorbing large amounts of wound exudate. An infected wound typically exudes large amounts of exudate, and the dressing must be capable of properly handling such exudate.

The polyurethane foam may e.g. be produced from a composition comprising a prepolymer based on hexamethylene diisocyanate (HDI), toluene diisocyanate (TDI) or methylene diphenyl diisocyanate (MDI).

The adhesive layer may also be referred to as a "wound contact layer" or a "skin contact layer". Preferably, the adhesive layer of the dressing comprises a silicone based adhesive. Such an adhesive is skin-friendly and permits the removal of the dressing without causing damage to the skin. The adhesive layer has a skin-facing surface and an opposing surface. The opposing surface faces the backing layer of the dressing. The opposing surface may be arranged in contact with the backing layer or the absorbent pad, where present.

The release liner 206 may be formed from one or more release liner portions. In FIG. 2, the release liner comprises two release liner portions 206*a-b*.

In the context of a dressing, the release liner may comprise a material selected from polyethylene, polyester, polypropylene and silicone coated paper. For example, the release liner may be a polyethylene film having a thickness in the range of from 30 to 300 μm, e.g. from 50 to 150 μm.

The antimicrobial coating may be provided as a discontinuous or a continuous coating on at least a portion of the skin-facing surface 203 of the adhesive layer 202.

Depending on the mode of application of the coating, the coating may be discontinuous; i.e. not fully covering the skin-facing surface of the adhesive layer, or continuous.

A continuous coating may be provided by dipping or soaking the adhesive layer in an aqueous solution comprising chlorhexidine phosphate.

A discontinuous coating 204 is generally preferred to avoid impairing the adhesion to the skin afforded by the adhesive layer 202.

The concentration of chlorhexidine phosphate in the antimicrobial coating 204 may be from 5 to 1000 $\mu g/cm^2$, e.g. from 10 to 500 $\mu g/cm^2$, e.g. from 20 to 200 $\mu g/cm^2$. In embodiments, the concentration of chlorhexidine phosphate in the antimicrobial coating 204 is from 50 to 200 $\mu g/cm^2$, e.g. from 10 to 130 $\mu g/cm^2$, e.g. from 20 to 100 $\mu g/cm^2$.

This secures the release of chlorhexidine phosphate in an amount sufficient to yield an antimicrobial effect at the wound site.

Figure 3:
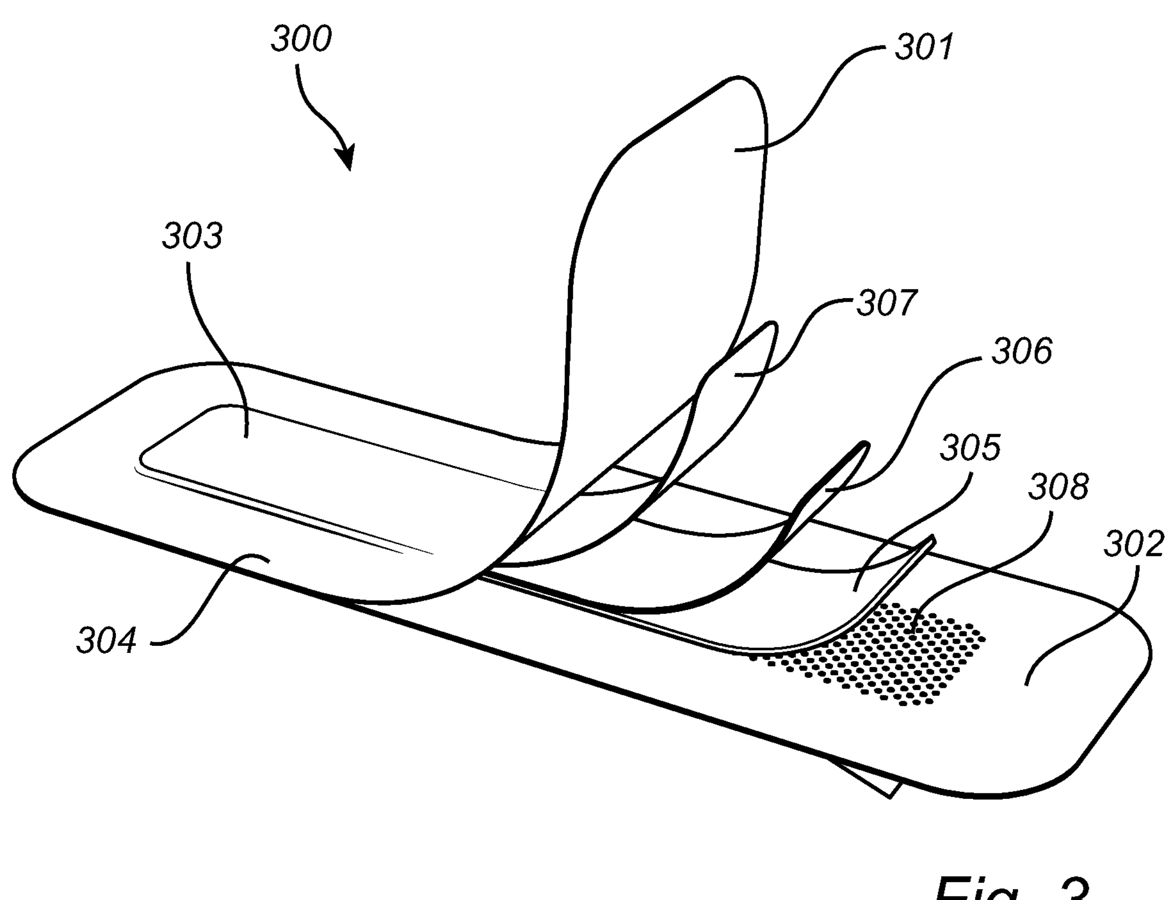
FIG. 3 illustrates a schematic perspective view of a dressing according to an exemplary embodiment of the present disclosure, wherein the dressing comprises a plurality of pad-forming layers.

In FIG. 3, a so called "border dressing" is illustrated. The dressing 300 may comprise a backing layer 301, an adhesive layer 302 and an absorbent pad 303 arranged between the backing layer 301 and the adhesive layer 302. The backing layer 301 and the adhesive layer 302 are configured to extend beyond the contour of the absorbent pad 303 to form a border portion 304.

The absorbent pad may be formed from a single layer or a plurality of pad-forming layers. The absorbent pad is not limited to a particular material, but typically comprises an absorbent foam or a gel. It may also comprise a superabsorbent material e.g. superabsorbent polymers (SAP) or superabsorbent fibers (SAF).

In exemplary embodiments, the absorbent pad comprises two or more layers having different properties laminated together.

As illustrated in FIG. 3, the absorbent pad 303 may comprise a first absorbent layer 305, a liquid distributing layer 306 and a second absorbent layer 307. Typically, the liquid distributing layer 306 is arranged between the first 305 and the second 307 absorbent layer, wherein the first absorbent layer 305 is the lowermost layer of the absorbent pad.

The first absorbent layer 305 may comprise a foam. Suitable foam materials for use in the first absorbent layer 305 include, but are not limited to polyurethane foams.

The second absorbent layer 307 may be a superabsorbent layer. Accordingly, the second absorbent layer may comprise superabsorbent polymers (SAP) or superabsorbent fibres (SAF).

The liquid distributing layer 306 may comprise any material having the ability to distribute the exudate in an efficient manner. For example, the liquid distributing layer 306 may comprise a nonwoven material. A nonwoven imparts an appropriately balanced rigidity to the layer and to the dressing as such. It may also efficiently distribute and spread liquid absorbed by the absorbent layer 305 such that it can be evaporated through the backing layer 301 over a large surface. For example, the nonwoven may comprise viscose, polyester or blends thereof.

The layers can be joined by adhesion, lamination, using e.g. pressure and heat.

The absorbent pad may comprise additional layers, such as liquid transport layers, various combinations of foam and nonwoven layers laminated together.

With reference to FIG. 3, the layer 305 may comprise an absorbent foam, the layer 306 may be a liquid acquisition layer, and the layer 307 may be a superabsorbent layer.

Such a layered pad construction prevents accumulation of body liquids close to the skin and improves the liquid handling of the dressing. Most wounds will contain some exudate, but the level of exudate may vary. In a chronic wound, the exudate production may be very large due to an ongoing inflammation. A dressing having the construction as explained above is suitable for handling large amounts of exudate and for preventing maceration of the skin surrounding the wound. Thus, the dressing is particularly suited for infection prevention.

The adhesive layer 302 may be a laminate comprising at least one polymeric film and an adhesive silicone layer, wherein the adhesive silicone layer is arranged to contact the skin or the wound.

The polymeric film simplifies the manufacturing process and provides stability and integrity to the adhesive layer 302.

The polymeric film is preferably a breathable film and may comprise e.g. polyethylene, polyamide, polyester or polyurethane. Preferably, the polymeric film comprises polyurethane. The thickness of the polyurethane film may be from 15 to 100 μm, e.g. from 20 to 80 μm, preferably from 20 to 60 μm.

Examples of suitable silicone gels for use in the adhesive silicone layer of the adhesive layer 302 and/or in the adhesive layer 202 described with respect to FIG. 2 include the two component RTV systems, such as Liveo MG-7-9960 (DuPont), and SilGel 612 (Wacker Chemie AG) mentioned herein, as well as NuSil silicone elastomers. In embodiments of the invention the adhesive may comprise a soft silicone gel having a softness (penetration) of from 8 to 22 mm, e.g. from 12 to 17 mm, as measured by a method based on ASTM D 937 and DIN 51580, the method being described in European Patent Application No 14194054.4. The thickness of the adhesive layer is typically at least 20 μm. The thickness of the adhesive layer may be from 30 to 200 μm.

As illustrated in FIG. 3, the adhesive layer 302 may comprise a plurality of apertures 308. The apertures 308 extend through the adhesive skin contact layer 302. The apertures 308 allow for a quick absorption into the pad 303 without compromising the tight fit to the skin provided by the adhesive layer 302. The adhesive skin contact layer 302 comprises a plurality of apertures 308 in the area underlying the absorbent pad 303, but is void of apertures in the area forming the border portion 304. The lack of apertures in the border portion of the dressing is beneficial to improve the adhesion at the border portion 304 of the dressing and thereby improve the stay-on ability of the dressing.

The apertures 308 may have different shapes and densities along varying regions of the adhesive skin contact layer 302, and may be arranged in a regular or irregular pattern.

The soluble antimicrobial coating comprising chlorhexidine phosphate is typically provided on the non-apertured parts of the skin-facing surface of the adhesive layer (not shown). Preferably, the antimicrobial coating is provided at least in the area of the adhesive layer underlying the absorbent pad 303.

In the various embodiments described hereinbefore, the backing layer may be a thin film, sheet or membrane that is vapor permeable. Examples of suitable materials for the backing layer include, but are not limited to polyurethane, polyethylene or polyamide films, silicone films, polyester based nonwoven materials, and laminates of polyester-based nonwoven materials and polyurethane films. Suitably, the backing layer is a polyurethane film having a thickness of from 5 to 40 μm, e.g. from 15 to 25 μm.

In order to enhance the antimicrobial effect, additional layers or components of the dressing may comprise an antimicrobial compound. For example, in embodiments, the absorbent pad 303 comprises at least one second antimicrobial compound. Alternatively, at least one of the pad-forming layers of the absorbent pad 303 comprises at least one second antimicrobial compound.

Alternatively, or in addition, the adhesive layer 302 comprises at least one third antimicrobial compound.

The at least one second and third antimicrobial compound may be the same or different.

Any antimicrobial compound suitable for incorporation in the pad or in the adhesive layer may be used. In embodiments, the second and/or third antimicrobial compound may be selected from the group comprising a silver salt, a chlorhexidine salt, polyhexamethylene biguaninde, benzethonium chloride, polidiallyldimethylammonium chloride etc.

In embodiments, the second and/or third antimicrobial compound is a silver salt, e.g. sulfate.

In embodiments, the second and/or third antimicrobial compound is chlorhexidine phosphate.

In embodiments, the at least one second antimicrobial compound is incorporated in the absorbent pad or in a pad-forming layer. For example, the at least one second antimicrobial compound may be incorporated into a foam layer of the absorbent pad of FIG. 3 or into the foam pad illustrated in FIG. 2. The at least one second antimicrobial compound may e.g. be chemically bound to the structure or internal surface, such as the pores, of the foam. The second antimicrobial compound may e.g. be bound to a charged internal surface of the foam.

It is also conceivable that the second antimicrobial compound is incorporated into the foam by adding the second antimicrobial compound to the pre-polymer before the foaming process step. This way, the antimicrobial compound may become integrated into the foam and bound within the cell walls of the foam.

Alternatively, the at least one second antimicrobial compound is provided as a coating on a layer of the absorbent pad, optionally prior to joining or lamination with one or more pad-forming layers or other layers of the pad.

Alternatively, the foam is impregnated with the at least one second antimicrobial compound. This way, a coating of the second antimicrobial compound onto a surface of the foam may be provided. This mode of application may also provide a coating of the second antimicrobial compound on the internal pore surfaces of the foam.

In embodiments, at least one third antimicrobial compound is integrated in the adhesive skin contact layer. In this case, the third antimicrobial compound may be added to an uncured mixture of silicone gel adhesive, and the adhesive mixture is subsequently cured. Additional excipients configured to facilitate the release of the at least one third antimicrobial compound may also be added.

The concentration of the second and/or third antimicrobial compound is typically higher than the concentration of chlorhexidine phosphate in the antimicrobial coating. The second and/or third antimicrobial compound may have a slower release profile and thereby provide a more long-term antimicrobial effect.

Figure 4A:
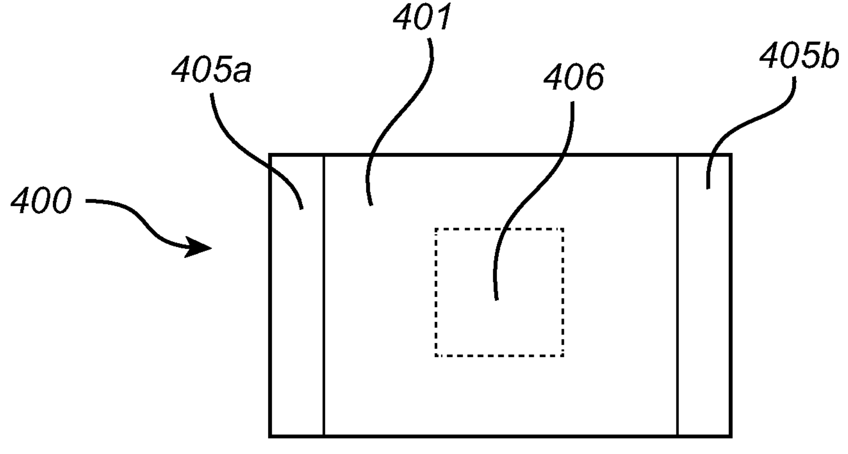
FIG. 4*a* schematically illustrates an incision drape according to an exemplary embodiment of the present disclosure
Figure 4B:
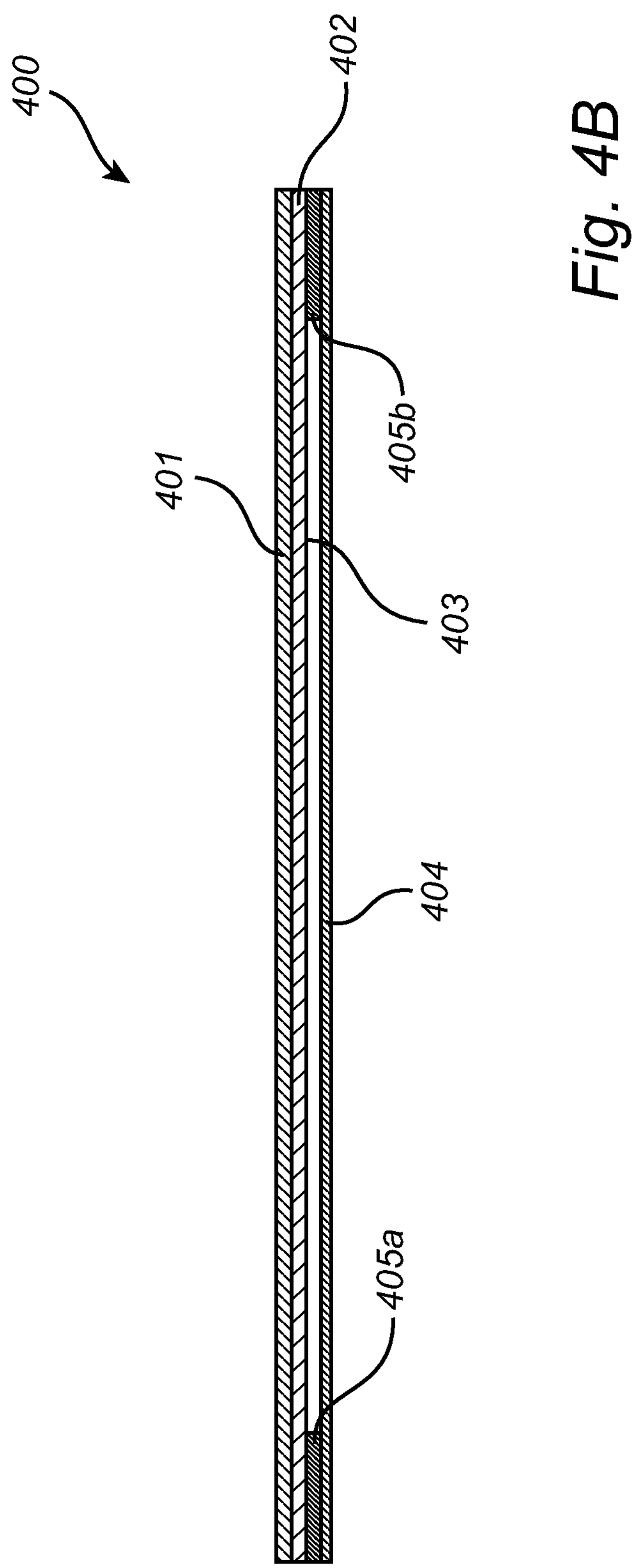
FIG. 4*b* illustrates a cross-sectional view of the incision drape in FIG. 4*a*.

In FIGS. 4*a* and 4*b*, a wound care product according to an exemplary embodiment is conceptually illustrated. The wound care product is, in FIG. 4, an incision drape 400, and the area 406 schematically illustrates where the drape is to be cut through during a surgical procedure.

As used herein, the term "incision drape" means a surgical drape used during surgery, and which is designed to be cut through. The incision drape, which may also be referred to as a "surgical incision drape" is attached to the patient's skin and isolates the surgical site from non-sterile areas that could increase the risk for surgical site infections.

As illustrated in FIG. 4*b*, the incision drape 400 comprises a backing layer 401 and an adhesive layer 402 having a skin-facing surface 403, wherein at least a portion of the skin-facing surface 403 of the adhesive layer 402 comprises an antimicrobial coating (not shown), wherein the antimicrobial coating is soluble in an aqueous medium and wherein the antimicrobial coating comprises chlorhexidine phosphate.

The antimicrobial coating is advantageously used on an incision drape and during surgery to prevent and combat contaminating microorganisms from infecting the incision site.

The term "backing layer" as used in the context of a surgical drape, e.g. an incision drape herein means a top layer of the wound care product; i.e. the layer facing away from the skin of a patient. The backing layer of the drape may e.g. comprise polyurethane, polyester and/or polypropylene.

The adhesive layer 402 may comprise any suitable adhesive and is by no means limited to a particular type of adhesive. Typically, the adhesive used is a silicone based adhesive or a polyacrylate based adhesive. Preferably, in the case of an incision drape, the adhesive layer 402 comprises a polyacrylate adhesive.

The materials of the backing layer 401 and the adhesive layer 402 are adapted to facilitate cutting through each of the layers of the drape.

As illustrated in FIG. 4, the incision drape comprises a release liner 404 configured to be removed prior to application of the drape. The release liner 404 is detachably attached to the adhesive layer. In FIG. 4, the release liner 404 has the same cross-sectional area as that of the backing layer 401. It is also conceivable that the release liner 404 has a larger cross-sectional area in order to facilitate removal from the drape prior to use.

As illustrated in FIG. 4*a*, the margins of the adhesive layer 402 may form handle portions 405*a-b* that the caregivers can grasp to remove the release liner 404 from the adhesive layer 402. A surgical drape typically has a relatively large size and often requires the aid of two caregivers to handle. One caregiver may grasp the first handle portion 405*a* of the drape, while the other caregiver may grasp the second handle portion 405*b* and remove the release liner gradually from the adhesive layer, thereby exposing the adhesive surface. The incision drape is then applied to the patient and subsequently smoothened out to prevent the formation of wrinkles. The handle portions 405*a-b* may be formed from any material. For example, a polymeric film, such as polyethylene may be utilized. The release liner 404 is not adhesively attached to the handle portions 405*a-b*. This is to facilitate removal of the release liner 404 from the adhesive layer 402.

The release liner 404 is not limited to a particular material, but any material known to the skilled person may be utilized. In embodiments, the release liner comprises silicone coated paper or polyester liners.

The antimicrobial coating prevents contaminating microorganism from migrating into the incision or wound site. Prior to application, the skin is typically cleansed to prevent contamination, however, the pores may still contain bacteria, which can migrate to the incision site. Accordingly, the antimicrobial coating prevents surgical site contamination.

Figure 5:
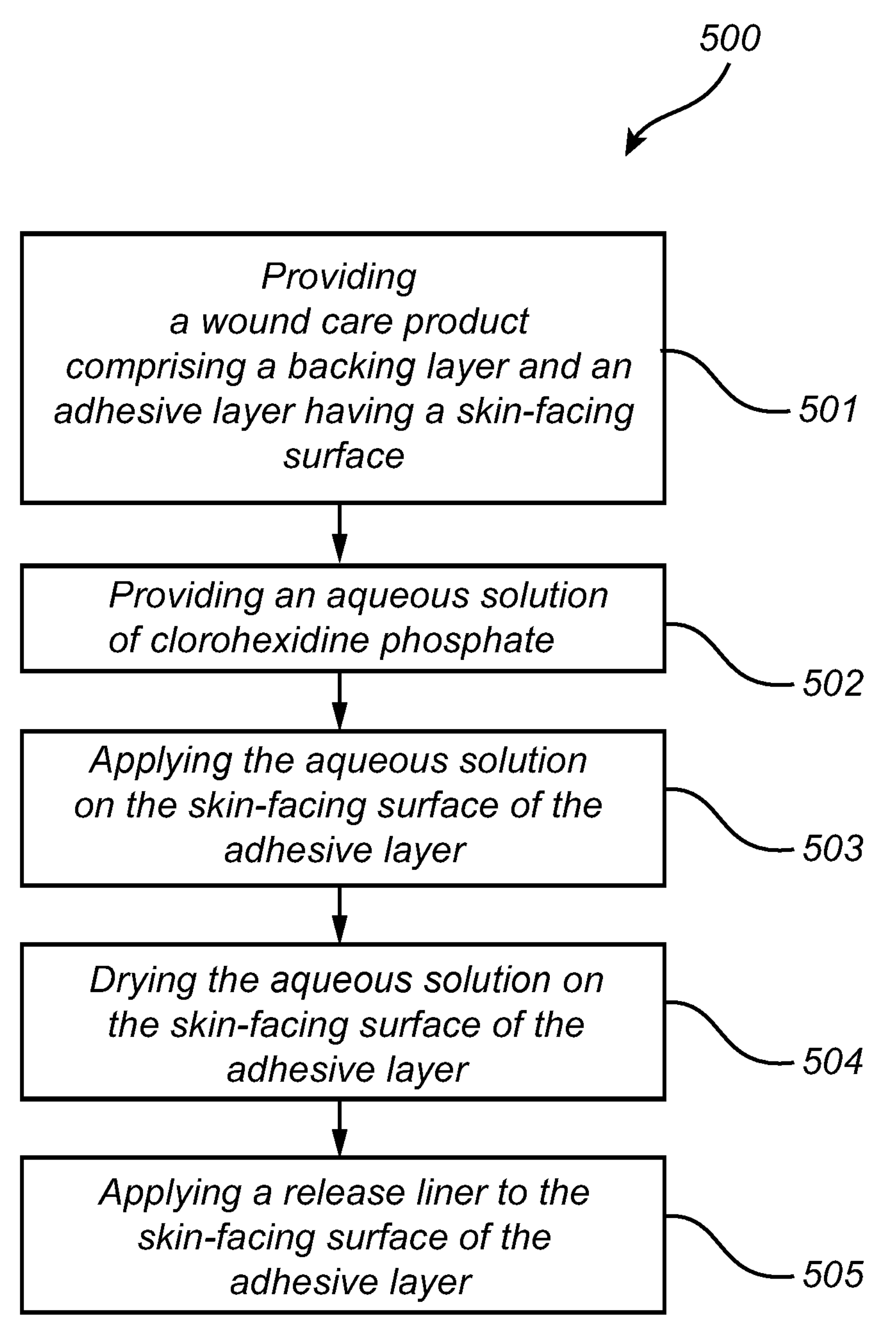
FIG. 5 schematically outlines the steps of the method according to an exemplary embodiment of the present disclosure.

With reference to FIG. 5, a second aspect of the present disclosure is schematically illustrated, covering a method for manufacturing a wound care product.

The method comprises:

a) providing a wound care product comprising a backing layer and an adhesive layer having a skin-facing surface, wherein the wound care product optionally comprises an absorbent pad arranged between the backing layer and the adhesive layer (step 501), b) providing an aqueous solution of chlorhexidine phosphate by dissolving chlorhexidine in phosphoric acid and water (step 502), c) applying the aqueous solution on at least a portion of the skin-facing surface of the adhesive layer (step 503), d) drying the aqueous solution on the skin facing surface of the adhesive layer (step 504).

The wound care product may be provided by means known to the skilled person. The assembly of the backing layer, the adhesive layer, and the absorbent pad, where present, is not limited to a particular method, but any means (e.g. adhesive bonding, lamination etc.) may be utilized.

The aqueous solution of chlorhexidine phosphate is provided by dissolving chlorhexidine in phosphoric acid and water. The solution may be mixed, and optionally stirred to secure complete dissolution of the salt.

The step of applying the aqueous solution on at least a portion of the skin-facing surface of the adhesive layer may be achieved with any coating technique.

Preferably, the aqueous solution is applied onto at least a portion of the skin facing surface of the adhesive layer by means of spray coating.

This coating technique is beneficial as it allows for flexibility depending on the dressing or substrate to be used and depending on the type of wound to be treated. It is also a simple means to apply the coating. Selected areas of the adhesive layer may be coated and the size of the droplets on the surface may be controlled to avoid interfering with the adhesive properties of the adhesive skin contact layer.

Drying is performed by means well known to the skilled person. For example, the coating may be heated to enhance the evaporation of liquid from the coating.

The pH of the aqueous solution of chlorhexidine phosphate may be from 4 to 6.

A pH in this range renders an unfavorable environment for infectious microorganisms to grow and colonize.

The molar ratio of chlorhexidine:phosphate in the aqueous solution may be from 1:1 to 1:3, preferably 1:2.

Accordingly, the salt is completely dissolved in the aqueous solution, with substantially no undissolved particles. If the ratio is too low, the solubility will decrease. In contrast, if the ratio is too high, the solution applied may not comprise enough active agent.

The method may further comprise the step of:

e) applying a release liner to the skin-facing surface of the adhesive layer (step 505).

EXAMPLES

Example 1

Antimicrobial Effect of CHP

Test organisms: *P. aeruginosa* ATCC 9027 (bacteria), *S. aureus* ATCC 6538 (bacteria), *C. albicans* ATCC 10231 (fungi), *P. aeruginosa* ATCC PAO1 (bacteria, example 1b).

Test time: 24 h for bacteria and 48 h for fungi

Start inoculum: 1×10^6 CFU/ml for bacteria, 4×10^6 CFU/ml for fungi.

Example 1a

Minimum Concentration Required to Eliminate Microorganism in Solution

Tests were performed in solution to compare the potency of silver sulfate, chlorhexidine phosphate and chlorhexidine gluconate, using simulated wound fluid, SWF (fetal bovine serum (FBS) and Peptone Water (PW) mixed in equal proportions, which correspond to the protein and electrolyte concentration of wound exudates (Emiko Aiba-Kojima, M D et. al Wound Rep Reg (2007) 15 511-520; Trengove, N et al Wound Rep Reg (1996) 4 1067-1927)) as test medium. The aim was to define the lowest concentration of an antimicrobial agent required to kill the specific microorganism. The test microorganisms were suspended in SWF, in which antimicrobial substances were added at different concentration before subculture in well microtiter plates. Positive and negative controls were used to demonstrate adequate microbial growth over the course of the incubation period and media sterility.

The results showed that up to 190 times more silver than chlorhexidine phosphate was required to kill *Candida albicans*. Chlorhexidine phosphate (CHP) was the most efficient antimicrobial, compared to both silver sulfate and chlorhexidine gluconate (CHG) (see table 1 below).

TABLE 1

| MBC comparison | | | |
|---|---|---|---|
| | Minimum bactericidal concentration (MBC) in μM | | |
| Microorganism | Silver sulfate | CHP | CHG |
| *S. aureus* | 310 | 7 | 30 |
| *P. aeruginosa* (ATCC 9027) | 160 | 26 | 520 |
| *Candida albicans* | 5000 | 26 | 60 |

Example 1b

Reduction of Biofilm Counts in Contact with CHP Solution

Tests were performed in solution to evaluate the potency of chlorhexidine phosphate (CHP) against biofilms cultured on a collagen matrix, using SWF as test medium. The aim was to define if concentrations of CHP that can be spray coated on the surface of the silicone contact layer would have an impact on the biofilms. The test microorganism was Pseudomonas aeruginosa PAO1, suspended in a SWF solution, and placed on a collagen matrix in wells of 24-well plates. The well plates were incubated at 37° C., 95% relative humidity for 24 h to induce formation of biofilms. After incubation and formation of biofilms, the antimicrobial substance CHP was added on top of biofilms at different concentrations in triplicates and were incubated for another 24 h at 37° C., 95% relative humidity. Positive and negative controls were used to demonstrate adequate biofilm growth over the course of the incubation period and media sterility. The number of viable counts were determined by plating on PetriFilms.

The results, illustrated in table 2 below show that the concentrations of CHP solutions of 37 μM, 75 μM, 150 μM, which are concentrations that can be achieved by spraying the silicone contact layer, reduced the amount of biofilms, and showed a log reduction higher than the FDA requirement of reduction 4. Accordingly, chlorhexidine phosphate (CHP) is an efficient antimicrobial substance against bacterial biofilms, especially compared to e.g. silver sulfate, which has a low potency against biofilms.

TABLE 2

| Reduction of biofilm at various CHP concentrations | | | | |
|---|---|---|---|---|
| Sample | Control | 1 | 2 | 3 |
| Concentration of CHP (uM) | 0 | 37 | 75 | 150 |
| Equivalent concentration if sprayed on surface (ug/cm2) | 0 | 18 | 36 | 73 |
| Log count | 10.0 | 4.4 | 3.9 | 4.1 |
| Log reduction | n/a | 5.5 | 6.1 | 5.9 |
| Standard deviation | 0.0 | 1.1 | 0.5 | 0.5 |

Example 1c

Antimicrobial Effect of CHP Sprayed on Silicone Surface

Tests were performed on coated and sterilized wound contact layers in order to compare the potency of prototypes coated with 75 μg/cm$^2$ of silver sulfate, with prototypes coated with 45 μg/cm$^2$, and 75 μg/cm$^2$ of chlorhexidine phosphate. The prototypes were punched into disks of 7 cm$^2$ and placed in a well in contact with 2 ml SWF containing a solution of microorganism in suspension (same microorganisms as used in Example 1a). The wound contact layer used in the tests comprised a polyurethane film coated with 200 gsm of a silicone adhesive.

The silver sulfate and the CHP coating were applied to the silicone surface by spray coating (Ultrasonic nozzle (120 kHz) from Sono-Tek).

Positive and negative controls were used to demonstrate adequate microbial growth over the course of the incubation period and media sterility. Microorganism growth was evaluated on the silicone layer; i.e. the skin facing surface, and in suspension in the liquid.

The chlorhexidine phosphate prototypes sprayed at a concentration of 45 μg/cm$^2$ and 75 μg/cm$^2$ presented full elimination of all microorganism both on the silicone surface and in the solution. As silver sulfate did not even achieve log 4 reduction from inoculum size against *Staphylococcus aureus* it was not evaluated further against other microorganisms.

Example 2

Transfer of Antimicrobial Agent to Release Liner

Tests were performed on coated and sterilized wound contact layers in order to compare the transfer of antimicrobial to the release liner.

The wound contact layer used in the tests comprised a polyurethane film coated with 200 gsm of a silicone adhesive.

The comparison was made between prototypes coated with an antimicrobial solution of chlorhexidine phosphate (0.56% by weight) and prototypes sprayed with the antimicrobial solution of chlorhexidine gluconate (0.56% by weight). Spraying was performed with the same parameters and with the same equipment as described in Example 1. After spraying, the samples were sent to sterilization on the production site to undergo typical sterilization cycle required for antimicrobial products.

After sterilization, the sterilized samples were observed by light microscopy (Olympus Zoom high-end stereo microscope SZH). The results showed that only minor transfer of chlorhexidine phosphate (CHP) was observed from the silicone surface of the wound contact layer to the release liner (see FIGS. 6*a*-6*b*). However, for the wound contact layer coated with chlorhexidine gluconate (CHG), the majority of the CHG coating transferred to the release liner, with some areas of the skin-facing surface showing close to full transfer, leaving large parts silicone area denuded of antimicrobial CHG (see FIGS. 6*c*-6*d*).

To more fully understand the transfer of the antimicrobial, the sterilized samples were punched into disks of 7 cm$^2$. Triplicates of silicone coated films (wound contact layers) and release liners were separated and placed in wells in contact with 2 ml solution of water during a time period evaluated to allow full dissolution of the antimicrobial particles of CHP and CHG. After calibration of the equipment against the solutions of interest, the concentration of CHP and CHG in the different wells was evaluated by Liquid chromatography-mass spectrometry to quantify the amount of antimicrobial agent present on the silicone and the amount that transferred to the release liner.

The results showed that after sterilization, more than 66% of the CHP spray coated on the wound contact layer was present on the silicone surface and therefore available for antimicrobial activity. Less than 36% of the CHG sprayed remained on the silicone, and the majority of the CHG (more than 64%) transferred to the release liner. Accordingly, the antimicrobial effect was significantly lost when the release liner was removed.

Example 3

Presence of CHP on Incision Drape Observed in Light Microscopy

Tests were also performed on incision drapes (921014-00 BNS Incise Drape from Mölnlycke Health Care) spray coated with CHP in order to identify potential transfer of antimicrobial to the release liner. One prototype was used in the tests, and the adhesive surface (comprising a polyacrylate based adhesive) of the incision drape was sprayed with a solution of CHP (0.56% by weight) utilizing the same spraying equipment and spraying equipment as described in Examples 1-2 hereinbefore. After drying, the sample was observed in light microscopy (Olympus Zoom high-end stereo microscope SZH). The results showed that a high concentration of CHP was present on the incision drape surface when the release liner had been removed (see FIG. 7).

Example

Rate of Dissolution of Antimicrobial Coating

Tests were performed on coated and sterilized wound contact layers in order to evaluate the rate of dissolution of the antimicrobial coating; i.e. release of the antimicrobial compound. The comparison was made between prototypes spray coated with an antimicrobial solution of chlorhexidine phosphate (0.56% by weight) and prototypes spray coated with an antimicrobial solution of chlorhexidine acetate (0.68% by weight). The spray coating was performed with the same parameters and on the same equipment, as described with respect to Example 1 and 2 hereinbefore. After spraying, the samples were sent to sterilization on production site to undergo typical sterilization cycle required for antimicrobial products.

After sterilization, the prototypes were punched into disks of 7 $cm^2$. Triplicates of silicone coated films (wound contact layers) and release liners were separated and placed in wells in contact with 2 ml solution of water during 3 hours, then removed and placed in a new well for 24 hours in order to evaluate instant (>3 h) and short (>24 h) term dissolution.

After calibration of the equipment against the solutions of interest, the concentration of CHP and CHAc in the different wells was evaluated by Liquid chromatography-mass spectrometry in order to quantify the amount of antimicrobial coating that was able to dissolve instantly or shortly.

CHP had an instant dissolution; i.e. an instant release from the silicone surface. 100% of the CHP was dissolved after 3 hours, while only 28% of the CHAc was dissolved after 3 hours, and less than 40% was dissolved after 24 h.

TABLE 3

Release of antimicrobial CHP and CHAc coatings

| | Instant dissolution % Released from silicone after 3 h | Short time dissolution Additional % released from silicone after additional 21 h | Total released in 24 h |
|---|---|---|---|
| CHP | 100% | — | 100% |
| CHAc | 28% | 11% | 39% |

These tests demonstrate that CHP has a quick rate of dissolution and therefore enables a rapid release and a rapid antimicrobial effect, compared to e.g. CHAc which has a slower rate of dissolution.

Example 5

Wear Test/Tackiness Test

Tests were performed to evaluate the impact on tackiness of the samples sprayed with chlorhexidine phosphate (CHP). Tack or tackiness is the property of a material that allows it to adhere to a surface immediately upon contact. The rolling ball tack test (ASTM D 3121-06) was used to evaluate the tackiness. In this test, the displacement of a metal ball on the silicone surface is measured.

The tack rolling ball test was performed on sterilized wound contact layers (as described hereinbefore) sprayed with chlorhexidine phosphate at 15, 45, and 75 μg/$cm^2$, respectively.

As illustrated in table 4 below, no significant impact on the tackiness was observed even at the higher concentrations of chlorhexidine phosphate (CHP). A non-coated sterilized wound contact layer was used as control.

TABLE 4

Effect of tackiness of wound contact layer at different CHP concentrations

| Prototype (sterile) | Control | CHP | CHP | CHP |
|---|---|---|---|---|
| Theoretical concentration (ug/cm2) | none | 15 | 45 | 75 |
| Tackiness (displacement in mm) | 11.2 +/- 22% | 13 +/- 4% | 15 +/- 0% | 16 +/- 5% |

Example 6

Transfer of CHP from the Release Liner

Additional tests were carried out to further evaluate the transfer of chlorhexidine phosphate from the wound contact layer to the release liner.

The wound contact layer used in the tests comprised a polyurethane film coated with 50 gsm of a silicone adhesive.

The tests were performed as described in Example 2 with a few deviations: the CHP coating was applied to 50 gsm of a silicone adhesive by spray coating (Air Atomizing nozzle from Sprayin System Co.) followed by an in-line drying phase under hood. Furthermore, the sample size of each specimen was 3,1 cm2 and the test was performed on 4 specimens. The wound contact layer and its release liner were separated and placed in wells with 1 ml water for 24 h.

As in example 2, Liquid chromatography-mass spectrophotometer (LCMS) was used to quantify the amount of antimicrobial agent (CHP) present on the wound contact layer; i.e. on the silicone adhesive, as well as the amount of transferred CHP to the release liner.

As illustrated in table 5 below, essentially all CHP remain on the wound contact layer after sterilization. Very little or no CHP was transferred to the release liner when the surface concentration of CHP on the wound contact layer was in the range between 28-92 μg/cm2.

TABLE 5

| Presence of CHP on wound contact layer, and release liner, respectively | | | |
|---|---|---|---|
| Surface concentration of CHP on silicone adhesive layer [$\mu g/cm^2$] | CHP on release liner [$\mu g/cm^2$] | Amount CHP present on silicone adhesive layer after extraction [%] | Transferred CHP [%] |
| 28 | <LOD (limit of detection) | 100 | 0% |
| 43 | <LOD | 100 | 0% |
| 44 | <LOD | 100 | 0% |
| 92 | 2 | 98 | 2% |

Example 7

Antimicrobial Effect for Samples Comprising a CHP Coating and a Silver Containing Polyurethane Foam Suspensions of 106 CFU/mL of *P. aeruginosa* (PaO1) and *S. aureus* (ATCC6838) respectively, were prepared in heat-inactivated SWF and inoculated into a well plate in a volume of 145 uL. Three replicates of each sample with the size of 2,5 cm2, were applied on top of each inoculum with the wound contact layer facing the inoculum and incubated at 35° ° C. for 24 h.

Each of the samples tested comprised a polyurethane foam and a wound contact layer containing a polyurethane film provided with a silicone adhesive layer. The wound contact layer was adhesively attached to the polyurethane foam. In some of the samples, the polyurethane foam comprised silver in an amount of about 1.2 mg/cm2 (samples A and B as explained hereinbelow). The CHP coating was applied to the wound contact layer; i.e. the silicone adhesive layer, by spray coating with a concentration of approximately 45 $\mu g/cm^2$. The spray coating was performed with the same parameters and on the same equipment, as described with respect to Example 6 hereinbefore.

Microorganism growth was evaluated in the whole sample, i.e. the wound contact layer and the silver containing foam.

Sample A comprised a silver containing polyurethane foam provided with an adhesive wound contact layer comprising a coating of CHP.

Sample B comprised a silver containing polyurethane foam provided with an adhesive wound contact layer comprising no antimicrobial coating.

Sample C comprised a polyurethane foam without any antimicrobial, provided with an adhesive wound contact layer comprising no antimicrobial coating.

Figure 8A:
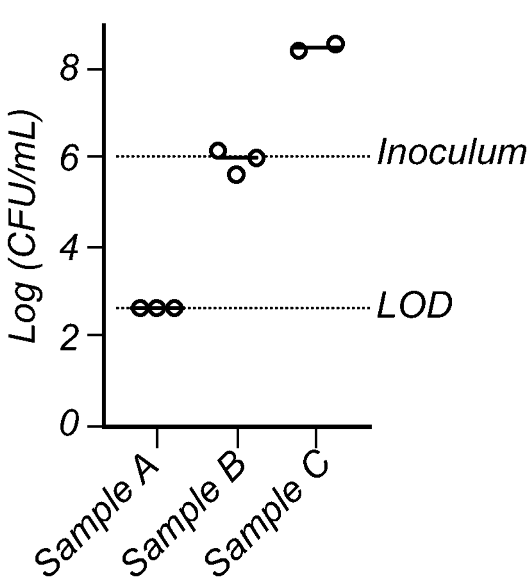
FIG. 8*a* illustrates the antimicrobial effect on *P. aeruginosa* (PaO1) with samples comprising a polyurethane foam and a wound contact layer with and without an antimicrobial coating comprising chlorhexidine phosphate as well as with and without silver in the polyurethane foam.

As illustrated in FIG. 8*a,* full elimination of *P. aeruginosa* was observed for samples containing silver in the polyurethane foam and CHP coated on the wound contact layer (sample A). Accordingly, a combined effect in having silver in the foam and CHP in the coating was observed. With these testing conditions, the bacterial concentration remained at inoculum size for samples containing silver in the polyurethane foam and without CHP on the wound contact layer (sample B). Accordingly, the presence of silver in the foam inhibited proliferation of *P. aeruginosa,* however, did not manage to reduce the bacterial number as sample A. The control samples without antimicrobials (sample C) reached a bacterial count of about Log 8, which is a two Log increase from start inoculum.

Figure 8B:
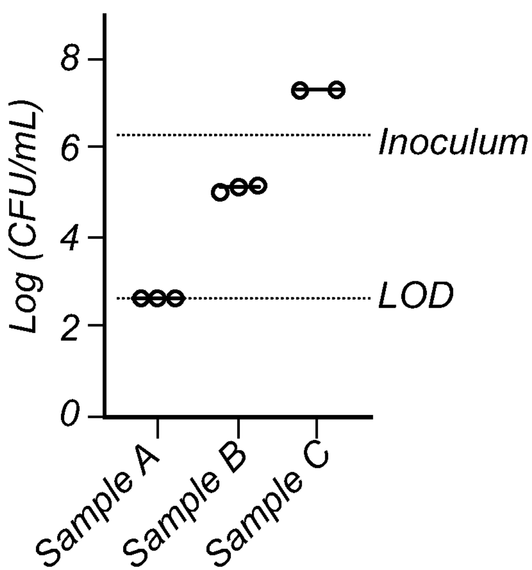
FIG. 8*b* illustrates the antimicrobial effect on *S. aureus* (ATCC6538) with samples comprising a polyurethane foam and a wound contact layer with and without an antimicrobial coating comprising chlorhexidine phosphate as well as with and without silver in the polyurethane foam.

A similar combined effect was observed for *S. aureus* (see FIG. 8*b*).

Terms, definitions and embodiments of all aspects of the present disclosure apply mutatis mutandis to the other aspects of the present disclosure.

Even though the present disclosure has been described with reference to specific exemplifying embodiments thereof, many different alterations, modifications and the like will become apparent for those skilled in the art.

Variations to the disclosed embodiments can be understood and effected by the skilled addressee in practicing the present disclosure, from a study of the drawings, the disclosure, and the appended claims. Furthermore, in the claims, the word "comprising" does not exclude other elements or steps, and the indefinite article "a" or "an" does not exclude a plurality.

The invention claimed is:

1. A wound care product comprising a backing layer and an adhesive layer having a skin-facing surface, wherein at least a portion of said skin-facing surface of said adhesive layer comprises an antimicrobial coating, characterized in that said antimicrobial coating is soluble in an aqueous medium and in that said antimicrobial coating comprises silicone and chlorhexidine phosphate, wherein the concentration of chlorhexidine phosphate in said antimicrobial coating is from 5 to 1000 $\mu g/cm^2$, wherein at least 60% of said antimicrobial coating dissolves within 3 hours of exposure to water, wherein said wound care product comprises a release liner, and wherein said release liner is detachably attached to said skin-facing surface of said adhesive layer.

2. The wound care product according to claim 1, wherein said wound care product is a dressing or a surgical drape.

3. The wound care product according to claim 1, wherein said antimicrobial coating is a discontinuous coating on said skin-facing surface of said adhesive layer.

4. The wound care product according to claim 1, wherein said wound product is a dressing and wherein said dressing further comprises an absorbent pad arranged between said backing layer and said adhesive layer.

5. The wound care product according to claim 4, wherein said absorbent pad comprises at least a second antimicrobial compound.

6. The wound care product according to claim 1, wherein said adhesive layer comprises at least a third antimicrobial compound.

7. The wound care product of according to claim 1, wherein the chlorhexidine phosphate is the only antimicrobial compound in the antimicrobial coating.

8. The wound care product according to claim 1, wherein the concentration of chlorhexidine phosphate in said antimicrobial coating is from 10 $\mu g/cm^2$ to 150 $\mu g/cm^2$.

9. The wound care product according to claim 1, wherein 100% of said antimicrobial coating dissolves within 3 hours of exposure to water.

10. A method of manufacturing the wound care product according to claim 1, the method comprising:

a) providing a wound care product comprising a backing layer and an adhesive layer having a skin-facing surface, wherein said wound care product comprises an absorbent pad arranged between said backing layer and said adhesive layer, b) providing an aqueous solution of chlorhexidine phosphate by dissolving chlorhexidine in phosphoric acid and water, c) applying said aqueous solution onto at least a portion of said skin-facing surface of said adhesive layer, d) drying said aqueous solution on said skin facing surface of said adhesive layer; and e) applying a release liner to said skin-facing surface of said adhesive layer.

11. The method according to claim 10, wherein the pH of said aqueous solution of chlorhexidine phosphate is from 4 to 6.

12. The method according to claim 10, wherein the molar ratio of chlorhexidine: phosphate in said aqueous solution is from 1:1 to 1:3.

13. The method according to claim 10, wherein said aqueous solution is applied onto at least a portion of said skin facing surface of said adhesive layer by means of spray coating.

* * * * *